United States Patent [19]

Tarpila et al.

[11] Patent Number: 5,478,819

[45] Date of Patent: Dec. 26, 1995

[54] PHOSPHOLIPID COMPOSITION AND USE THEREOF

[75] Inventors: Simo Tarpila, Välskärinkatu 5 A 8, SF-00290 Helsinki; Anneli Kivinen, Tampere, both of Finland

[73] Assignee: Simo Tarpila, Helsinki, Finland

[21] Appl. No.: 80,126

[22] Filed: Jun. 23, 1993

[51] Int. Cl.$^6$ .......................... A61K 31/43; A61K 37/22
[52] U.S. Cl. .......................... 514/192; 514/198; 514/199; 424/450
[58] Field of Search .......................... 424/450; 514/925, 514/926, 927, 200, 198, 192, 29, 152, 78, 199

[56] References Cited

U.S. PATENT DOCUMENTS

| | | | |
|---|---|---|---|
| 4,918,063 | 4/1990 | Lichtenberger | 514/78 |
| 5,000,958 | 3/1991 | Fountain et al. | 424/450 |
| 5,077,057 | 12/1991 | Szoka, Jr. | 424/450 |
| 5,169,637 | 12/1992 | Lenk et al. | 424/450 |
| 5,196,205 | 3/1993 | Borody | 424/653 |
| 5,229,380 | 7/1993 | Harris | 514/152 |

FOREIGN PATENT DOCUMENTS

| | | |
|---|---|---|
| 0092121 | 10/1983 | European Pat. Off. . |
| 0249561 | 12/1987 | European Pat. Off. . |
| 0287198 | 10/1988 | European Pat. Off. . |
| 0401952 | 12/1990 | European Pat. Off. . |
| WO9218181 | 11/1992 | WIPO . |

OTHER PUBLICATIONS

Kivinen et al., Kivinen, Phospholipids, Milchwissenschaft 47(11) 1992, pp. 694–696.
Kivinen et al., Kivinen, Phospholipids, Milchwissenschaft 47(9) 1992, pp. 573–575.

*Primary Examiner*—Raymond Henley, III
*Attorney, Agent, or Firm*—Birch, Stewart, Kolasch & Birch

[57] ABSTRACT

A method of and composition for treating a *Helicobacter pylori* infection in a mammal. The method comprises administering to said mammal orally a therapeutically effective amount of a *Helicobacter pylori* eradicating antibiotic and a phospholipid. The composition comprises a *Helicobacter pylori* eradicating antibiotic and a phospholipid.

12 Claims, No Drawings

PHOSPHOLIPID COMPOSITION AND USE THEREOF

FIELD OF THE INVENTION

The present invention relates to a method for treating a *Helicobacter pylori* infection, a composition for use in the said method, as well as a method of manufacturing the said composition.

BACKGROUND OF THE INVENTION

During the past decade it has been shown that the infection induced by *H. pylori* is the single most important factor in the development of gastritis. Gastritis induced by *H. pylori* is in fact one of the most common bacterial infections in the world. The infection causes an inflammation in the mucosa of the stomach, which, in some cases, slowly leads to the atrophy of the mucosa (atrophic gastritis).

A *Helicobacter pylori* infection is in itself symptomless. However, it predisposes the infected subject to ulcer diseases of the stomach and of the duodenum, and it also slightly increases the risk of stomach cancer. Once infected, the patient may carry the inflammation through his life, due to the lack of effective natural defense. After the infection, the same bacterial strain continues to grow inside the mucous layer on the surface of the mucous membrane.

The present treatment of *H. pylori* infection is based on the combination of one or more antibiotics together with bismuth preparations. Agents inhibiting gastric acid secretion ($H_2$-blockers and omeprazole) are also used for *H. pylori* eradication treatment. The treatment is difficult and, to be at all successful, it requires strong motivation and patience from both the patient and the doctor.

Combination therapy usually gives better *H. pylori* eradication than single drug therapy. Triple therapy (e.g. antibiotic/metronidazole/bismuth) for example, has been found to give better results than single drug therapy. One common combination used contains metronidazole (1200 mg/d), amoxicillin (1500 mg/d), and tetracycline (1550 mg/d), administered for two weeks and followed by bismuth subcitrate (480 mg/d) for four weeks. The other antibiotics used have usually been selected from the group consisting of ampicillin, penicillin, minocycline, doxycycline, erythromycin, clindamycin and ofloxacin, optionally in combination with metronidazole, tinidazole or furazolidone (*Helicobacter pylori* in Peptic Ulceration and Gastritis, ed. Marshall B. J. et al., Blackwell Scientific Publications, 1991, USA)

The problems associated with the present treatment relate to the development of resistant *H. pylori* strains, the reappearance of *H. pylori* after treatment, the long duration of the treatment and several side-effects (e.g. diarrhea caused by *Clostridia difficile*). This leads also to poor patient compliance.

On the other hand, it is previously known that exogenous phospholipids are of importance in the protection of the gastrointestinal tract (Lichtenberger et al., Science 219, 1327–1329, (1983)). It is assumed that the phospholipid molecules attach to the cell membranes with electrostatic bonds and direct their fatty acid side chains into the lumen, thus forming a uniform hydrophobic surface (Hills et al., Am. J. Physiol. 244, G561–G568 (1983)). Lichtenberger (EP publications 401 952 and 287 198) discloses methods employing compositions composed of mixtures of phospholipids and neutral lipids to treat the luminal lining of the gastrointestinal tract in the prevention or treatment of ulcerogenic processes. It is also generally well known to administer drugs, such as non-steroidal, anti-inflammatory drugs, together with phospholipids, and there is a number of publications relating thereto (e.g. DE 2856333). There is also a number of publications relating to the use of phospholipids of a specific composition for administration together with a variety of drugs for use in different manners of administration.

The phospholipid compositions have typically been formulated into colloidal or liposomal suspensions using an aqueous medium or diluent (EP publications 287 198). Especially liposome technology has advanced the delivery of drugs, diagnostic materials, cosmetics etc. Liposomes have been used to deliver drugs by encapsulating the drugs in the liposomes during their preparation, or alternatively, by combining the drugs with the liposomes following their formation (EP publication 249 561), and then administering them to the patient to be treated.

Liposomes are closed by one or several bilayer membranes containing an entrapped aqueous volume. The structure of the membrane bilayer is such that the hydrophobic 'tails' of the lipid orient toward the centre of the bilayer while the hydrophilic 'heads' orient towards the aqueous phase. The formation of a mixture of lipids into a bladder form can be accomplished by a number of ways, the original liposome preparation being disclosed by Bangham et al. (J. Mol. Biol. 13, 238–252, (1965)). The procedures used involve application of energy, such as by sonication or microfluidic procedures.

Liposomes prepared from synthetic phospholipids are of highest purity with required fatty acid composition and thus do not cause technical or analytical problems, as is the case with natural phospholipids. However, highly purified phospholipids of natural sources can be used.

However, there has so far been no effort to treat a *Helicobacter pylori* infection with a combination of phospholipid and a *H. pylori* eradicating antibiotic, prior to the present invention. The present inventors have now surprisingly discovered that a synergistic effect can be achieved in such a treatment.

SUMMARY OF THE INVENTION

It has now surprisingly been found that by combining a therapeutically effective amount of a *Helicobacter pylori* eradicating antibiotic and a phospholipid, it is possible to obtain a number of advantages in the oral treatment of a *Helicobacter pylori* infection.

DETAILED DESCRIPTION OF THE INVENTION

The present invention thus combines the advantages of phospholipids to a *H. Pylori* eradicating antibiotic, creating a surprising synergistic effect. When the patient is treated according to the present invention, the phospholipid-antibiotic composition is specifically carried to the desired site of action, where it decomposes releasing the drug on the surface of the mucosa and forming a protective layer thereon. The antibiotic is efficiently adsorbed locally by the mucosa, which allows the eradication of *H. pylori* with the use of considerably smaller doses of an antibiotic than the prior art treatment. This naturally leads to lesser side-effects wherefore the treatment can, if necessary, be longer, leading to the complete eradication of the *Helicobacter pylori* infection. This has not been possible earlier.

In addition to carrying the antibiotic to the site of action, the phospholipid composition of the invention also repairs the damaged mucosa and recovers the destroyed phospholipid layer. It creates a hydrophobic cover, which allows the antibiotic to give its complete effect under the said cover and which also prevents the back-diffusion of acid on the surface of the damaged mucosa. This prevention of acid back-diffusion is a further advantage of the present invention, since there is now no need to administer $H_2$-blockers or omeprazol to prevent the secretion of acids. Also the treatment with bismuth is unnecessary.

The method of treatment of a *Helicobacter pylori* infection in a mammal according to the present invention comprises administering to said mammal in need of such treatment orally a therapeutically effective amount of a *H. pylori* eradicating antibiotic and a phospholipid. Several *H. pylori* eradicating antibiotics or mixtures thereof may come in question, such as those selected from the group of metronidazole, tinidazole, furazolidone, amoxicillin, ampicillin, penicillin, tetracycline, minocycline, doxycycline, erythromycin, clindamycin, gentamicin, nitrofurantoin, rifampicin, ofloxacin, ciprofloxacin, cefalexin, cefoxitin, imipenem, thiamphenicol, sulfonamides, vancomycin and clarithromycin. Advantageously, metronidazole, amoxicillin and tetracycline are used, as well as erythromycin as an alternative for patients allergic to penicillin.

The phospholipids used in the method according to the invention are selected from the group consisting of phosphatidylcholines, phosphatidylethanolamines, phosphatidylserines, phosphatidylinositols, sphingomyelins and mixtures thereof. Preferably synthetic phospholipids are used. According to a preferred embodiment, the phospholipid is phosphatidylcholine, such as dipalmitoylphosphatidylcholine. According to a further embodiment the phospholipid is used in admixture with cholesterol. The ratio between phospholipid, especially phosphatidylcholine and cholesterol may vary, but stable liposomes have been obtained with a weight ratio of 7:2.

This invention also relates to a composition for treating a *Helicobacter pylori* infection, comprising a therapeutically effective amount of a *Helicobacter pylori* eradicating antibiotic and a phospholipid, as well as a method of making the said composition.

The phospholipids of the composition according to the invention are characterized generally by the formula

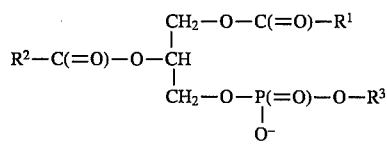

wherein $R^1$ and $R^2$ are independently selected from the group consisting of saturated and unsaturated alkyl groups, the groups $R^1$ and $R^2$ containing independently each approximately 5 to 21 carbon atoms, and $R^3$ is a group of the formula —$CH_2CH_2$—$N^+R_3$, wherein R is selected from hydrogen or lower alkyl (cholines), or $R^3$ is —$CH_2$—$CH(NH_2)$—COOH (serines),

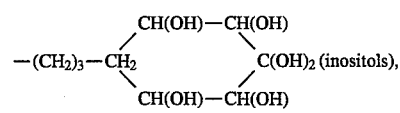

as well as salts thereof. Avantageous phospholipids of the composition according to the invention are those, wherein $R^1$ and $R^2$ independently contain 13 to 19 carbon atoms, are saturated or contain 1 or 2 double bonds. An advantageous specific phosphatidylcholine is dipalmitoylphosphatidycholine.

A preferred composition according to the invention has essentially the following phospholipid composition:

|  | W % |
| --- | --- |
| phosphatidylcholine | 20–60 |
| phosphatidylethanolamine | 10–40 |
| phosphatidylserine | 10–40 |
| phosphatidylinositol | 10–40 |
| sphingomyelin | 0–15 |

An especially preferred composition according to the invention has essentially the following phospholipid composition:

|  | W % |
| --- | --- |
| phosphatidylcholine | 45 |
| phosphatidylethanolamine | 32 |
| phosphatidylserine | 9 |
| phosphatidylinositol | 9 |
| sphingomyelin | 5 | which composition is close to the natural phospholipid composition of the gastrointestinal mucosa in mammals.

The composition has preferably essentially thet following fatty acid composition (expressed as mole-% of the fatty acid residues included in the said phospholipid composition):

| (C-atoms:double bonds) | mole % |
| --- | --- |
| palmitic (16:0) | 20–60 |
| palmitoleic (16:1) | 0–10 |
| stearic (18:0) | 5–30 |
| oleic (18:1) | 15–40 |
| linoleic (18:2) | 20–60 |

Especially preferred composition according to the invention has essentially the following fatty acid composition:

| (C-atoms:double bonds) | mole % |
| --- | --- |
| palmitic (16:0) | 30 |
| palmitoleic (16:1) | 2 |
| stearic (18:0) | 8 |
| oleic (18:1) | 16 |
| linoleic (18:2) | 44 |

The phospholipids to be used according to the invention are generally available commercially, but can also be prepared by methods known in the art.

The phospholipid composition is advantageously formed into liposome form, according to methods known to those skilled in the art. An extensive article on the subject is found in Szoka, F. et al Ann. ReV. Biophys. Bioeng. 1980 9:467–508. When the antibiotic is water soluble, the active agent is preferably located within the liposome, and in case of fat soluble active agents, in the liposome layer.

The composition according to the present invention may be administered in a form of liquid, suspension or powder.

In addition to a therapeutically effective amount of a *H. pylori* eradicating antibiotic and phospholipids, the composition according to the invention may contain additional agents, such as carriers, adjuvants, antioxidants, preservatives and taste improving agents, known to those skilled in the art.

The present invention also relates to a method of manufacturing a pharmaceutical for the treatment of a *Helicobacter pylori* infection using a composition comprising a therapeutically effective amount of a *Helicobacter pylori* eradicating antibiotic and a phospholipid, and optionally combining the same with a therapeutically acceptable carrier or adjuvant.

A method of treatment according to the invention comprises administering orally to mammals is need of treatment, a therapeutically effective amount of a *Helicobacter pylori* eradicating antibiotic and a phospholipid. In the preferred method the phospholipid is in liposome form containing the antibiotic.

The method of treatment according to the invention comprises administering the said antibiotic preferably in an amount which varies from 1/10 to the normal dose/day for a period of at least one week. The absolute amount to be administered naturally depends on the specific antibiotic and the condition to be treated, and can easily be determined by a person skilled in the art. The amount of phospholipid used in the method of treatment according to the invention is 300–3000 mg/day.

The composition according to the invention can also be administered in combination with other therapeutically active agents, optionally those used previously in the treatment of a *Helicobacter pylori* infection.

The following examples illustrate the invention but are not intended to be limiting.

EXAMPLE 1

General preparation of a Liposome Formulation

Phospholipids and cholesterol are dissolved in chloroform in a weight ratio of 7:2, and dried in a rotary evaporator to form a thin lipid film. The antibiotic is suspended in a buffer solution and added to the flask containing the lipid film. The molar ratio of antibiotic to lipid is 1:2. The film is then dispersed in the antibiotic-buffer by vortex-mixing and sonicating under a nitrogen atmosphere. The temperature is chosen to be the highest transition temperature of the phospholipids used. The liposome drug suspension is washed in the same buffer by centrifugating at 4000 rpm for 20 min in order to separate associated antibiotic from non-associated antibiotic. The liposome-drug suspension is the filtered through a membrane filter. The liposome suspension obtained is stored protected from air and light.

In the above mentioned manner a liposome preparation can be made from dipalmitoylphosphatidylcholine and cholesterol containing ampicillin or tetracycline. The dose of ampicillin and tetracycline can vary 150–1500 mg/day administered 2–4 times a day, for a period of 1–2 weeks. Similarly meronidazol is administered 120–1200 mg/day (given 2–3 times a day) for a period of 1–2 weeks.

We claim:

1. A method of treating *Helicobacter pylori* infection in a mammal, said method comprising orally administering a liposome composition comprising phospholipid and an effective amount of ampicillin or amoxycillin or penicillin, or mixtures thereof, to said mammal in need of such treatment.

2. The method according to claim 1 comprising administering said ampicillin or amoxycillin or penicillin, or mixtures thereof in an amount of 1/10 to the normal dose a day for a period of at least one week.

3. The method according to claim 1 comprising administering said phospholipid in an amount of 300–3000 mg/day.

4. The method according to claim 1, wherein said phospholipid is selected from the group consisting of phosphatidylcholines, phosphatidylethanolamines, phosphatidylserines, phosphatidylinositols, sphingomyelins and mixtures thereof.

5. The method according to claim 1, wherein said phospholipid is in admixture with cholesterol.

6. The method according to claim 5, wherein said phospholipid is phosphatidylcholine.

7. The method according to claim 5, wherein said phosphatidylcholine and cholesterol are in a weight ratio of 7:2.

8. The method according to claim 1, wherein said phospholipid is of the formula

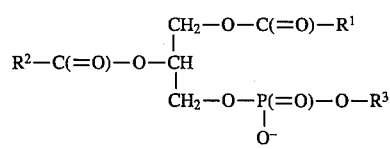

wherein $R^1$ and $R^2$ are independently selected from the group consisting of saturated and unsaturated alkyl groups containing 5 to 21 carbon atoms, and $R^3$ is a group of the formula $-CH_2CH_2-N^+R_3$, wherein R is selected from hydrogen or lower alkyl, or $R^3$ is $-CH_2-CH(NH_2)-COOH$,

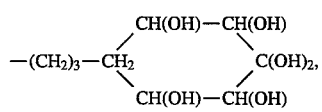

and salts thereof.

9. The method according to claim 8, wherein $R^1$ and $R^2$ independently contain 13 to 19 carbon atom.

10. The method according to claim 1, wherein said phospholipid consists of a mixture of

|  | W % |
| --- | --- |
| phosphatidylcholine | 20–60 |
| phosphatidylethanolamine | 10–40 |
| phosphatidylserine | 10–40 |
| phosphatidylinositol | 10–40 |
| sphingomyelin | 0–15. |

11. The method according to claim 9, wherein $R^1$ and $R^2$ independently are saturated.

12. The method according to claim 9, wherein $R^1$ and $R^2$ independently contain 1 or 2 double bonds.

\* \* \* \* \*